US012746534B2

(12) United States Patent
Wang et al.

(10) Patent No.: US 12,746,534 B2
(45) Date of Patent: Sep. 29, 2026

(54) HYDROGENATION CATALYSTS AND METHOD FOR BENZOIC ACID HYDROGENATION REACTION

(71) Applicant: Hunan Changlian New Material Technology Co., Ltd., Yueyang City (CN)

(72) Inventors: Hui Wang, Yueyang City (CN); Minglin Xiang, Yueyang City (CN); Xichun She, Yueyand City (CN); Bo Ao, Yueyang City (CN); Hongsheng Kuang, Yueyang City (CN)

(73) Assignee: HUNAN CHANGLIAN NEW MATERIAL TECHNOLOGY CO., LTD., Yueyang City (CN)

( * ) Notice: Subject to any disclaimer, the term of this patent is extended or adjusted under 35 U.S.C. 154(b) by 559 days.

(21) Appl. No.: 18/258,131

(22) PCT Filed: Nov. 25, 2021

(86) PCT No.: PCT/CN2021/133095
§ 371 (c)(1),
(2) Date: Jun. 16, 2023

(87) PCT Pub. No.: WO2022/127550
PCT Pub. Date: Jun. 23, 2022

(65) Prior Publication Data

US 2024/0058797 A1 Feb. 22, 2024

(30) Foreign Application Priority Data

Dec. 18, 2020 (CN) ......................... 202011513693.6

(51) Int. Cl.
*B01J 23/89* (2006.01)
*B01J 37/08* (2006.01)
(Continued)

(52) U.S. Cl.
CPC ........... *B01J 23/8946* (2013.01); *B01J 37/08* (2013.01); *B01J 37/16* (2013.01); *C07C 51/36* (2013.01)

(58) Field of Classification Search
CPC .... B01J 37/0201; B01J 37/0207; B01J 37/08; B01J 37/088; B01J 37/16; B01J 23/89;
(Continued)

(56) References Cited

U.S. PATENT DOCUMENTS 3,210,411 A * 10/1965 Mars ....................... C07C 51/36 585/469
2012/0296111 A1* 11/2012 Konigsmann .......... B01J 35/392 502/262

(Continued)

FOREIGN PATENT DOCUMENTS

CN 1775353 A 5/2006
CN 101092349 A 12/2007

(Continued)

OTHER PUBLICATIONS

Jia et al. "Confined NiRu Bimetallic Catalysts for the Hydrogenation of Dimethyl Terephthalate to Dimethyl Cyclohexane-1,4-dicarboxylate", Ind. Eng. Chem. res. 2019, 58, pp. 22702-22708 (Year: 2019).*

(Continued)

*Primary Examiner* — Tam M Nguyen
(74) *Attorney, Agent, or Firm* — CANTOR COLBURN LLP

(57) ABSTRACT

Disclosed are hydrogenation catalysts and a method for a benzoic acid hydrogenation reaction. The hydrogenation catalysts comprise a carrier, and an active component, an
(Continued)

auxiliary component, and an alkali metal element that are loaded on the carrier. The active component is ruthenium. The auxiliary component is one or two or more of nickel, iron and cobalt. The method for the hydrogenation reaction comprises a first hydrogenation step and a second hydrogenation step. A first hydrogenation catalyst and a second hydrogenation catalyst are the hydrogenation catalyst. The hydrogenation catalysts according to the present invention have high catalytic activity at a low temperature, and can react under relatively mild reaction conditions. The hydrogenation reaction method according to the present invention can implement the continuous and stable operation of a device, and meets industrial-scale operation requirements.

15 Claims, 1 Drawing Sheet

(51) Int. Cl.
*B01J 37/16* (2006.01)
*C07C 51/36* (2006.01)

(58) Field of Classification Search
CPC .... B01J 23/8946; B01J 21/063; B01J 21/066; B01J 21/08; B01J 21/18; C07C 51/36; C07C 2601/14
USPC .......................................................... 502/326
See application file for complete search history.

(56) References Cited

U.S. PATENT DOCUMENTS

| | | | | |
|---|---|---|---|---|
| 2015/0183699 | A1* | 7/2015 | Hembre | C07C 29/149 568/831 |
| 2015/0183706 | A1* | 7/2015 | Hembre | C07C 51/36 562/509 |

FOREIGN PATENT DOCUMENTS

| | | | |
|---|---|---|---|
| CN | 105251482 | A | 1/2016 |
| CN | 106554281 | A | 4/2017 |
| CN | 106984310 | A | 7/2017 |
| CN | 107649147 | A | 2/2018 |
| CN | 107774257 | A | 3/2018 |

OTHER PUBLICATIONS

Internatioanl Search Report for PCT/CN2021/133095 filed on Nov. 25, 2021, 3 pages.
Jiang, et al., "Solid state synthesis of Ru-MC with highly dispersed semi-embedded ruthenium nanoparticles in a porous carbon framework for benzoic acid hydrogenationt", The Royal Society of Chemistry 2016, 8 pages.
Shinde, et al., "Catalytic Hydrogenation of Benzoic Acid", INTECH, 2017, Chapter 6, 8 pages.
Zhang, et al., "One-pot synthesized mesoporous C—TiO2 hybrid for Rucatalyzed low-temperature hydrogenation of benzoic acid", J Mater Sci (2019) 54:7529-7540, 12 pages.

* cited by examiner

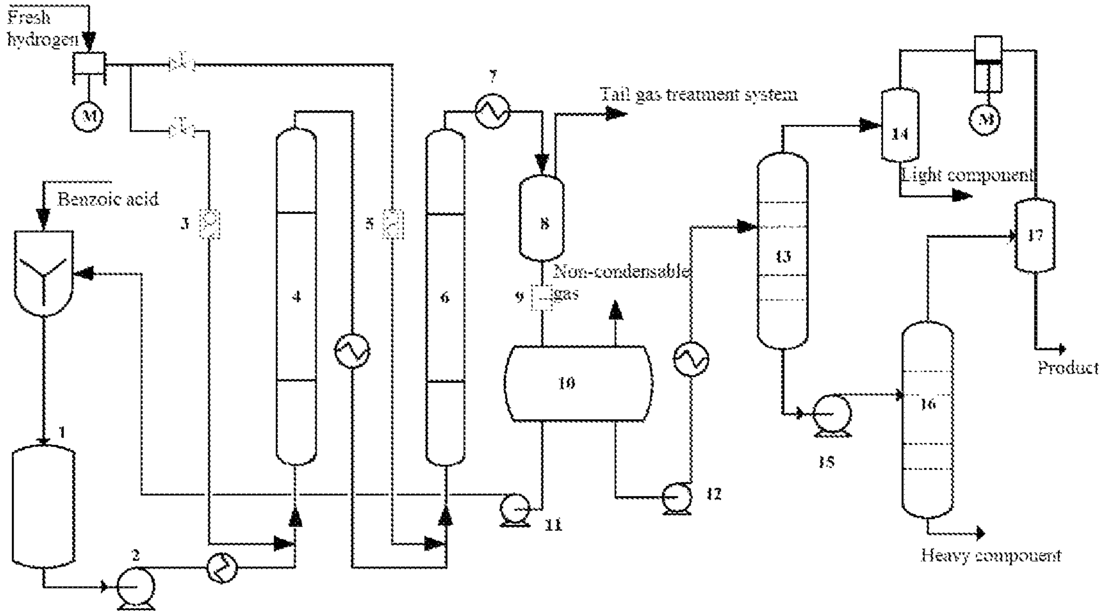
Fresh hydrogen
M
Benzoic acid
1
2
3
4
5
6
7
Tail gas treatment system
8
9
Non-condensable gas
10
11
12
13
14
Light component
M
15
16
Heavy component
17
Product

HYDROGENATION CATALYSTS AND METHOD FOR BENZOIC ACID HYDROGENATION REACTION

CROSS REFERENCE TO RELATED APPLICATIONS

This application claims the benefit of Chinese patent application 202011513693.6, filed on Dec. 18, 2020, the contents of which are incorporated herein by reference.

FIELD OF THE INVENTION

The present invention relates to a hydrogenation catalyst, and further relates to a method for a benzoic acid hydrogenation reaction using the hydrogenation catalyst.

BACKGROUND OF THE INVENTION

Cyclohexylcarboxylic acid (i.e., 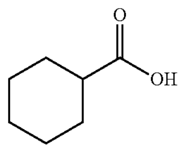 )

and derivatives thereof are important organic chemical raw materials and pharmaceutical intermediates, and have wide application values in drug synthesis and development of new materials. Cyclohexylcarboxylic acid is mainly used in the synthesis of a photoinitiator 184 (i.e., 1-carboxycyclohexylphenyl ketone), can also be used as a solubilizer for vulcanized rubber, a clarifier for petroleum, and a pharmaceutical intermediate, and used in the synthesis of an anti-pregnancy drug 392 and a drug praziquantel for treating schistosomiasis.

Cyclohexylcarboxylic acid can be prepared by hydrogenation of benzoic acid. Catalysts for the preparation of cyclohexylcarboxylic acid by hydrogenation of benzoic acid are mainly Pd/C or modified Pd/C catalysts, and a hydrogenation process mainly adopts a tank hydrogenation process.

CN101092349A discloses a method for hydrogenation of benzoic acid, comprising subjecting molten benzoic acid and hydrogen to a hydrogenation reaction in a reactor in the presence of a Pd/C catalyst and an Ru/C auxiliary, subjecting the resulting mixture to hydrocyclone separation and centrifugal separation after the reaction, recycling a turbid liquid comprising a high concentration of catalyst and auxiliary back to the reactor system, and allowing a separated clear liquid to enter an evaporator for further separation, wherein the catalyst and the auxiliary separated from the evaporator are completely returned to the reactor, wherein the hydrogenation reaction is carried out at a temperature of 120-180° C. The disadvantages of this method are as follows: first, the reaction activity of molten benzoic acid is low, the process conditions are severe, and the noble metal palladium is expensive; secondly, when the benzoic acid hydrogenation reaction is carried out by a tank reaction process, the process is complicated, and the product is in contact with the catalyst for a long time, so that secondary reactions are increased, the reaction selectivity is decreased, catalyst poisoning is also easily caused, and the service life of the catalyst is shortened; in addition, since a hydrogenation catalyst is typically in the form of powder, separation of the hydrogenation catalyst from reaction raw materials and products is difficult, and losses during filtration separation and catalyst regeneration are large, resulting in high unit consumption of the noble metal catalyst.

To sum up, it is urgent to develop a novel benzoic acid hydrogenation catalyst and a benzoic acid hydrogenation process.

SUMMARY OF THE INVENTION

The present invention aims to overcome the shortcomings in the prior art and provide a hydrogenation catalyst and a method for a benzoic acid hydrogenation reaction. The hydrogenation catalyst has high catalytic activity and enables hydrogenation in a fixed bed reactor under mild conditions, thereby achieving the continuous hydrogenation of benzoic acid.

According to a first aspect of the present invention, the present invention provides a hydrogenation catalyst, comprising carrier, and active component, auxiliary component and alkali metal element supported on the carrier, wherein the active component is ruthenium, and the auxiliary component is one or two or more selected from the group consisting of nickel, iron and cobalt.

According to a second aspect of the present invention, the present invention provides a method for benzoic acid hydrogenation reaction, comprising first hydrogenation step and second hydrogenation step, wherein

- in the first hydrogenation step, benzoic acid and hydrogen are in contact with first hydrogenation catalyst under conditions of first hydrogenation reaction to obtain first hydrogenation mixture; and
- in the second hydrogenation step, the first hydrogenation mixture and supplemental hydrogen are in contact with second hydrogenation catalyst under conditions of second hydrogenation reaction to obtain second hydrogenation mixture;
- wherein the first hydrogenation catalyst and the second hydrogenation catalyst are the same or different, and are each independently selected from a hydrogenation catalyst comprising carrier, and active component, auxiliary component and alkali metal element supported on the carrier, wherein the active component is ruthenium, and the auxiliary component is one or two or more selected from the group consisting of nickel, iron and cobalt.

The hydrogenation catalyst according to the present invention has high catalytic activity even at a low temperature, is used as a catalyst for a hydrogenation reaction of preparing cyclohexylcarboxylic acid from benzoic acid, enables a reaction to be carried out under relatively mild reaction conditions, and can obtain improved catalytic activity. The method for the benzoic acid hydrogenation reaction according to the present invention can implement the continuous and stable operation of a device, and meets industrial-scale operation requirements.

BRIEF DESCRIPTION OF DRAWINGS

FIG. 1 is used to illustrate a preferred embodiment of a method for a benzoic acid hydrogenation reaction according to the present invention.

| Description of reference signs | |
|---|---|
| 1: | Hydrogenation feedstock buffer tank |
| 2: | Metering pump |
| 3: | Flow controller |
| 4: | Main hydrogenation tubular reactor |
| 5: | Flow controller |
| 6: | Post-hydrogenation fixed bed reactor |
| 7: | Condenser |
| 8: | High-pressure separation tank |
| 9: | Control valve |
| 10: | Hydrogenation crude product tank |
| 11: | Metering pump |
| 12: | Metering pump |
| 13: | Light component removal column |
| 14: | Recovery tank |
| 15: | Pump |
| 16: | Heavy component removal column |
| 17: | Product tank |

DETAILED DESCRIPTION OF THE EMBODIMENTS

The endpoints and any values of the ranges disclosed herein are not limited to the precise range or value, and these ranges or values should be understood as including values close to these ranges or values. For numerical ranges, the endpoint values of each range, the endpoint values of each range and individual point values, and individual point values may be combined with each other to obtain one or more new numerical ranges, and these numerical ranges should be considered to be specifically disclosed herein.

According to a first aspect of the present invention, the present invention provides a hydrogenation catalyst, comprising carrier, and active component, auxiliary component and alkali metal element supported on the carrier, wherein the active component is ruthenium, and the auxiliary component is one or two or more selected from the group consisting of nickel, iron and cobalt.

According to the hydrogenation catalyst of the present invention, the active component is ruthenium. The content of the active component is preferably 0.3-3 wt %, for example, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 wt % based on the total amount of the hydrogenation catalyst, the active component is calculated by element. Preferably, the content of the active component is preferably 0.5-3 wt % based on the total amount of the hydrogenation catalyst. More preferably, the content of the active component is preferably 0.8-3 wt % based on the total amount of the hydrogenation catalyst.

According to the hydrogenation catalyst of the present invention, the auxiliary component is one or two or more selected from the group consisting of nickel, iron and cobalt. According to the hydrogenation catalyst of the present invention, ruthenium is used in combination with the auxiliary component, which synergistically act with each other to effectively promote the improvement of the catalyst activity. According to the hydrogenation catalyst of the present invention, the content of the auxiliary component is preferably 0.3-3 wt %, for example, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 wt % based on the total amount of the hydrogenation catalyst, the auxiliary component is calculated by element.

According to the hydrogenation catalyst of the present invention, in one preferred embodiment, a molar ratio of the auxiliary component to the active component is 0.1-25:1. According to this preferred embodiment, the catalytic activity of the hydrogenation catalyst can be further increased. According to this preferred embodiment, when the auxiliary component is nickel, the molar ratio of the auxiliary component to the active component is preferably 0.5-1.5:1, more preferably 0.8-1.2:1. According to this preferred embodiment, when the auxiliary component is cobalt, the molar ratio of the auxiliary component to the active component is preferably 0.1-0.5:1, more preferably 0.12-0.25:1. According to this preferred embodiment, when the auxiliary component is iron, the molar ratio of the auxiliary component to the active component is preferably 10-25:1, more preferably 15-20:1.

According to the hydrogenation catalyst of the present invention, the carrier is preferably one or two or more selected from the group consisting of activated carbon, silicon oxide, titanium oxide and zirconium oxide. In one preferred embodiment, the auxiliary component is nickel, and the carrier is activated carbon and/or titanium oxide. In another preferred embodiment, the auxiliary component is iron, and the carrier is zirconium oxide. In yet another preferred embodiment, the auxiliary component is cobalt, and the carrier is silicon oxide.

The hydrogenation catalyst according to the present invention also comprises alkali metal element, and the content of the alkali metal element may be 10-1000 ppm by weight, preferably 50-800 ppm by weight, more preferably 80-600 ppm by weight, further preferably 100-550 ppm by weight based on the total amount of the hydrogenation catalyst, the alkali metal element is calculated by element.

In the present invention, the content of the active component and the content of the auxiliary component in the hydrogenation catalyst are determined by X-ray fluorescence spectroscopy, and the content of the alkali metal element in the hydrogenation catalyst is determined by inductively coupled plasma emission spectroscopy.

The hydrogenation catalyst according to the present invention may be prepared by a method comprising the following steps of:

(1) contacting carrier with solution comprising alkali metal compound to obtain a modified carrier;

(2) contacting the modified carrier with solution comprising active component precursor and auxiliary component precursor to obtain a supported carrier supported with the active component precursor and the auxiliary component precursor, removing at least part of volatile components from the supported carrier, and performing calcination to obtain a hydrogenation catalyst precursor, wherein the calcination is carried out at a temperature of not higher than 300° C., active component of the active component precursor is ruthenium, and auxiliary component of the auxiliary component precursor is one or two or more selected from the group consisting of nickel, iron and cobalt; and (3) contacting the hydrogenation catalyst precursor with reducing agent under conditions of reduction reaction to obtain the hydrogenation catalyst.

According to the method for preparing the hydrogenation catalyst of the present invention, the catalytic activity of the hydrogenation catalyst can be significantly increased by contacting the carrier with the solution comprising the alkali metal compound to introduce alkali metal onto the carrier before supporting the carrier with the active component and the auxiliary component. According to the method for preparing the hydrogenation catalyst of the present invention, the content of the alkali metal element in the finally prepared hydrogenation catalyst may be 10-1000 ppm by weight, preferably 50-800 ppm by weight, more preferably 80-600 ppm by weight, further preferably 100-550 ppm by weight, the alkali metal element is calculated by element.

In the step (1), the alkali metal compound is preferably alkali metal hydroxide, more preferably one or two or more selected from the group consisting of sodium hydroxide, potassium hydroxide and lithium hydroxide, further preferably sodium hydroxide.

A solvent of the solution comprising the alkali metal compound may be water and/or $C_1$-$C_4$ alcohol, preferably water.

In the step (1), a method for contacting the carrier with the solution comprising the alkali metal compound may be a conventional method, for example, one or a combination of two or more of impregnation and spraying, preferably impregnation. The impregnation may be equal-volume impregnation or excessive impregnation. The number of times of the impregnation may be one or two or more times. When the number of times of the impregnation is two or more times, volatile components on the carrier may be removed after each impregnation.

The carrier may be in contact with the solution comprising the alkali metal compound under conventional conditions. In one preferred embodiment, the carrier is in contact with the solution comprising the alkali metal compound at a temperature of 20-60° C., for example, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60° C. A duration of the contacting may be 2-20 h, preferably 2-10 h.

In the step (1), after the carrier is in contact with the solution comprising the alkali metal compound, washing is performed. A solid material obtained after the contacting may be washed with water. The washing conditions are preferably such that a washing effluent (i.e., washing effluent water) has a pH value of 7.2-7.5.

Volatile components supported on a carrier supported with the solution which is obtained by contacting the carrier with the solution comprising the alkali metal hydroxide can be removed by a conventional method to obtain the modified carrier. Specifically, the carrier supported with the solution may be dried to obtain the modified carrier. The drying is preferably carried out at a temperature of less than 150° C. In one preferred embodiment, the drying is carried out at a temperature of 80-120° C. A duration of the drying may be 4-20 h, preferably 5-15 h. The drying may be carried out under atmospheric pressure (i.e., 1 atm) or may be carried out under reduced pressure conditions.

In the step (2), the active component is ruthenium. In the present invention, the term “active component precursor” refers to substance capable of forming active component in the catalyst during preparation of catalyst. The active component precursor is preferably one or two or more selected from the group consisting of ruthenium chloride, ruthenium nitrate and ruthenium acetate. The auxiliary component is one or two or more selected from the group consisting of nickel, iron and cobalt. In the present invention, the term “auxiliary component precursor” refers to substance capable of forming auxiliary component in the catalyst during preparation of a catalyst. The auxiliary component precursor is preferably one or two or more selected from the group consisting of nitrate, sulfate, formate, acetate and chloride of the auxiliary component, and specific examples of the auxiliary component precursor may include, but are not limited to, one or two or more selected from the group consisting of nickel nitrate, nickel sulfate, nickel acetate, nickel chloride, cobalt nitrate, cobalt sulfate, cobalt acetate, cobalt chloride, iron nitrate, iron sulfate, iron acetate, and iron chloride.

In the step (2), solvent of the solution comprising the active component precursor and the auxiliary component precursor may be water and/or $C_1$-$C_4$ alcohol, preferably water.

In the solution comprising the active component precursor and the auxiliary component precursor, the content of the active component precursor is preferably $1\times10^{-5}$ mol/mL to $20\times10^{-5}$ mol/mL, more preferably $1.1\times10^{-5}$ mol/mL to $15\times10^{-5}$ mol/mL, and the content of the auxiliary component precursor is preferably $0.5\times10^{-5}$ mol/mL to $15\times10^{-5}$ mol/mL, more preferably $1\times10^{-5}$ mol/mL to $10\times10^{-5}$ mol/mL, further preferably $2\times10^{-5}$ mol/mL to $8\times10^{-5}$ mol/mL. According to the method of the present invention, a molar ratio of the alkali metal compound employed in the step (1) to the total amount of the active component precursor and the auxiliary component precursor employed in the step (2) may be 1-8:1, preferably 1.5-6:1, more preferably 3-5:1.

According to the method for preparing the hydrogenation catalyst of the present invention, the active component precursor and the auxiliary component precursor are based on that the active component and the auxiliary component satisfying the requirements can be introduced onto the carrier.

In the step (2), a method for contacting the carrier with the solution may be a conventional method, for example, one or a combination of two or more of impregnation and spraying, preferably impregnation. The impregnation may be equal-volume impregnation or excessive impregnation. The number of times of the impregnation may be one or two or more times, which is based on that a sufficient amount of the active component and a sufficient amount of the auxiliary component can be introduced onto the carrier. When the number of times of the impregnation is two or more times, volatile components on the carrier may be removed after each impregnation.

In the step (2), the carrier may be in contact with the solution under conventional conditions. In one preferred embodiment, the carrier is in contact with the solution at a temperature of 40-80° C., for example, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80° C. A duration of the contacting may be 5-30 h, preferably 10-20 h, more preferably 15-20 h.

In the step (2), volatile components supported on the carrier supported with the solution which is obtained by contacting the carrier with the solution may be removed by a conventional method. Specifically, the carrier supported with the solution may be dried to obtain the modified carrier. The drying is preferably carried out at a temperature of less than 150° C. In one preferred embodiment, the drying is carried out at a temperature of 80-120° C. A duration of the drying may be 4-20 h, preferably 8-20 h. The drying may be carried out under atmospheric pressure (i.e., 1 atm) or may be carried out under reduced pressure conditions.

In the step (2), the calcination is carried out at a temperature of not higher than 300° C., for example 150-300° C. Preferably, the calcination is carried out at a temperature of not higher than 250° C. The calcination performed at a temperature of not higher than 250° C. can significantly increase the catalytic activity of the finally prepared hydrogenation catalyst compared with calcination performed at a higher temperature. More preferably, the calcination is carried out at a temperature of 150-250° C., for example, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250° C. A duration of the calcination may be 2-10 h. The calcination may be performed in an oxygen-containing atmosphere or in a reducing atmosphere.

According to the method for preparing the hydrogenation catalyst of the present invention, in the step (3), the reducing agent may be substance sufficient to reduce active component element and auxiliary component element in the hydrogenation catalyst precursor. In one preferred embodiment, the reducing agent is one or two or more selected from the group consisting of hydrazine hydrate, sodium borohydride and formaldehyde. In one preferred instance, the auxiliary component is nickel and/or iron, and the reducing agent is preferably hydrazine hydrate and/or formaldehyde. According to this preferred instance, when the reducing agent is hydrazine hydrate and formaldehyde, a molar ratio of hydrazine hydrate (hydrazine hydrate is calculated by hydrazine $N_2H_4$) to formaldehyde is preferably 1:2-6, more preferably 1:3-5. In another instance, the auxiliary component is cobalt, and the reducing agent is preferably sodium borohydride.

The amount of the reducing agent used may be selected by the content of the active component and the content of the auxiliary component in the hydrogenation catalyst precursor, which is based on that the active component and the auxiliary component in the hydrogenation catalyst precursor can be reduced. Generally, in terms of moles, a ratio of the reducing agent in the step (3) to (the active component in the step (2)+the auxiliary component in the step (2)) is 3-6:1 (i.e. a molar ratio of the reducing agent to the total amount of the active component precursor and the auxiliary component precursor in the step (2) is 3-6:1), the active component precursor is calculated by the active component and the auxiliary component precursor is calculated by the auxiliary component.

The reduction may be carried out at a temperature of 20-80° C., for example, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80° C. A duration of the reduction may be selected according to the temperature of the reduction and may be, for example, 1-10 h. In one preferred instance, the auxiliary component is nickel and/or cobalt, the reduction is carried out at a temperature of 50-80° C., and the duration of the reduction is preferably 1-5 h. In another preferred instance, the auxiliary component is iron, the reduction is carried out at a temperature of 20-40° C., and the duration of the reduction is preferably 6-10 h.

In the step (3), volatile components of the reduced catalyst precursor are removed to obtain the hydrogenation catalyst employed by the method of the present invention. The reduced catalyst precursor may be dried to remove the volatile components from the reduced catalyst precursor. The drying may be carried out at a temperature of 40-150° C., preferably at a temperature of 50-120° C., more preferably at a temperature of 60-100° C., further preferably at a temperature of 70-90° C. A duration of the drying may be selected according to the temperature of the drying and may generally be 5-24 h, preferably 6-20 h, more preferably 8-10 h. The drying may be carried out in an oxygen-containing atmosphere (such as an air atmosphere), or in a non-oxidizing atmosphere, such as a nitrogen atmosphere and/or a group zero gas atmosphere (such as argon). When drying is carried out in the oxygen-containing atmosphere, the drying is preferably carried out at a temperature of not more than 100° C., for example, at a temperature of 40-80° C., preferably at a temperature of 60-80° C. The drying may be carried out under atmospheric pressure (i.e., 1 atm) or under reduced pressure conditions, which is not particularly limited.

According to a second aspect of the present invention, the present invention provides a method for a benzoic acid hydrogenation reaction, comprising a first hydrogenation step and a second hydrogenation step, wherein in the first hydrogenation step, benzoic acid and hydrogen are in contact with first hydrogenation catalyst under conditions of first hydrogenation reaction to obtain first hydrogenation mixture; and in the second hydrogenation step, the first hydrogenation mixture and supplemental hydrogen are in contact with second hydrogenation catalyst under conditions of second hydrogenation reaction to obtain second hydrogenation mixture;

wherein the first hydrogenation catalyst and the second hydrogenation catalyst are the same or different, and are each independently selected from the hydrogenation catalyst described in the first aspect of the present invention.

According to the method for the benzoic acid hydrogenation reaction of the present invention, the first contacting and the second contacting may be carried out in a conventional reactor. In one preferred embodiment, the first contacting is carried out in tubular reactor, and the second contacting is carried out in fixed bed reactor. According to this preferred embodiment, continuous and convenient operation can be realized, an operation of separating a catalyst from a reactant which is necessary when a tank reactor is used can be avoided, and catalyst loss can be reduced. In the present invention, the fixed bed reactor refers to a reactor in which catalyst is packed in reaction zone of the reactor to form catalyst bed layer (ratio of inner diameter of the catalyst bed layer to total height of the catalyst packed within the reactor is typically greater than 1, preferably 3-10:1), and the tubular reactor refers to reactor in which two or more reaction tubes are arranged inside the reactor, and catalyst is packed in the reaction tubes (ratio of inner diameter of each reaction tube to total height of the catalyst packed in the reaction tube is typically less than 1). In this preferred embodiment, reaction feedstocks enter the reactor preferably from the bottom of the reactor and pass through the internal space of the reactor filled with the hydrogenation catalyst in a bottom-up manner.

According to the method for the benzoic acid hydrogenation reaction according to the present invention, the amount of hydrogen used in the first hydrogenation step and the amount of supplemental hydrogen used in the second hydrogenation step can be routinely selected. The catalyst used in the method for the hydrogenation reaction according to the present invention has high catalytic activity, and enables the hydrogenation reaction to be carried out continuously, and the method for the hydrogenation reaction according to the present invention can obtain a good hydrogenation reaction effect even at a low amount of hydrogen used. According to the method for the hydrogenation reaction of the present invention, a molar ratio of hydrogen to benzoic acid in the first hydrogenation step is preferably 2.4-4:1, for example, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1 or 4:1. According to the method for the hydrogenation reaction of the present invention, in the second hydrogenation step, a molar ratio of the supplemental hydrogen to benzoic acid in the first hydrogenation step is 1-3:1, for example, 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1 or 3:1.

According to the method for the hydrogenation reaction of the present invention, the first hydrogenation step and the second hydrogenation step may be carried out at conventional hydrogenation reaction temperatures. The hydrogenation catalyst used in the method for the hydrogenation reaction according to the present invention has good low-temperature hydrogenation reaction activity, and a good hydrogenation reaction effect can be obtained even when the hydrogenation reaction is carried out at a relatively low temperature. Preferably, in the first hydrogenation step, the contacting is carried out at a temperature of 60-90° C., for example, the contacting may be carried out at a temperature of 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90° C. In the second hydrogenation step, the contacting is carried out at a temperature of 80-120° C., for example, the contacting may be carried out at a temperature of 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 or 120° C.

According to the method for the hydrogenation reaction of the present invention, in the first hydrogenation step, the contacting is preferably carried out under a pressure of 1-5 MPa, the pressure being a gauge pressure. In the second hydrogenation step, the contacting is carried out under a pressure of 1-5 MPa, the pressure being a gauge pressure.

According to the method for the hydrogenation reaction of the present invention, a weight hourly space velocity of benzoic acid in the first hydrogenation step is preferably 0.5-6 $h^{-1}$. In the second hydrogenation step, a weight hourly space velocity is preferably 0.5-3 $h^{-1}$ in terms of benzoic acid in the first hydrogenation step.

According to the method for the hydrogenation reaction of the present invention, the first hydrogenation step and the second hydrogenation step are preferably carried out in the presence of at least one solvent. The solvent may be one or two or more selected from the group consisting of cyclohexanecarboxylic acid, ethanol and ethyl acetate, preferably cyclohexanecarboxylic acid. According to the method for the hydrogenation reaction of the present invention, benzoic acid may be mixed with the solvent to form a hydrogenation feedstock solution, and the hydrogenation feedstock solution and hydrogen are in contact with the first hydrogenation catalyst. According to the method for the hydrogenation reaction of the present invention, the content of benzoic acid in the hydrogenation feedstock solution may be 10-40 wt %.

According to the method for the hydrogenation reaction of the present invention, in the first hydrogenation step, benzoic acid and hydrogen may be premixed to be in contact with the first hydrogenation catalyst, or benzoic acid and hydrogen may be separately fed into hydrogenation reactor to be in contact with the first hydrogenation catalyst.

In one preferred embodiment, benzoic acid and hydrogen are premixed to be in contact with the first hydrogenation catalyst. According to this preferred embodiment, hydrogen may be mixed with benzoic acid and optionally a solvent by a conventional method to obtain the feedstock mixture. For example, hydrogen may be mixed with benzoic acid and optionally a solvent in a mixer, wherein the mixer may be one or a combination of two or more of a dynamic mixer and a static mixer. The static mixer achieves uniform mixing of gas and liquid by changing a flow state of a fluid, and may specifically be, but is not limited to, one or a combination of two or more selected from the group consisting of SV-type static mixer, SK-type static mixer, SX-type static mixer, SH-type static mixer and SL-type static mixer. The dynamic mixer may be a variety of mixing devices that achieve uniform mixing of gas and liquid through the movement of moving parts, such as common various parts having a stirring function.

In one preferred embodiment, hydrogen is injected into benzoic acid and optionally solvent through a gas-liquid mixer, thereby obtaining the feedstock mixture, wherein the gas-liquid mixer includes at least one liquid channel for accommodating the feedstock solution and at least one gas channel for accommodating the hydrogen, the liquid channel and the gas channel are adjoined by a member, and at least part of the member is a perforated area through which the hydrogen is injected into the feedstock solution. In the present invention, the term "liquid channel" refers to a space capable of accommodating a liquid phase stream; and the term "gas channel" refers to a space capable of accommodating hydrogen.

At least part of the member is a perforated area which extends along the length of the member. Preferably, the perforated area covers the entire member (i.e. the liquid channel and the gas channel are adjoined by a member having pores with an average pore size being nano-scaled, and the hydrogen is injected into the liquid phase stream through the pores). The perforated area has pores with an average pore size being nano-scaled such that hydrogen is injected into the liquid phase stream through the pores with the average pore size being nano-scaled.

In this preferred embodiment, the pores in the perforated area may be micro-pores and/or nano-pores. In the present invention, the term "micro-pores" refers to pores having an average pore size of more than 1000 nm, and the micro-pores preferably have an average pore size of not more than 600 more preferably not more than 500 In the present invention, the term "nano-pores" refers to pores having an average pore size of not more than 1000 nm, such as pores having an average pore size of 1 nm to 1000 nm. More preferably, the pores in the perforated area are nano-pores. Further preferably, the pores in the perforated area have an average pore size of 50 nm to 500 nm. The average pore size is determined by scanning electron microscopy.

The member may be one or a combination of two or more selected from the group consisting of a porous membrane, a porous plate, and a porous pipe. The porous pipe means that a wall of a channel is porous. An inner surface and/or an outer surface of the porous pipe may be attached with a porous membrane, in this way, a pore size of pores in the pipe can be adjusted, for example, the pores in the wall of the pipe may be micro-pores, and pores in the porous membrane attached to the inner surface and/or the outer surface of the pipe may be nano-pores, and in the present invention, the pipe of which the inner surface and/or the outer surface are/is attached with the porous membrane in which pores are nano-pores is also considered to be that pores in the perforated area are nano-pores. As an example of a pipe having a porous membrane, the porous pipe may be a membrane pipe. The number of channels in the porous pipe is not particularly limited, and generally, the number of the channels in the porous pipe may be 4-20.

The gas-liquid mixer may be disposed in a pipe conveying reaction feedstocks to achieve mixing with hydrogen during the conveying of the reaction feedstocks.

According to the method for the hydrogenation reaction of the present invention, the method further includes a separation step in which the second hydrogenation mixture is separated to obtain cyclohexylcarboxylic acid. The second hydrogenation mixture may be distilled to separate cyclohexylcarboxylic acid.

In one preferred embodiment, the separation step comprises first distillation and second distillation, wherein in the first distillation, the second hydrogenation mixture is distilled in a light component removal column under reduced pressure conditions to obtain a distillate comprising light components from the top of the light component removal column, and a bottom effluent from the bottom of the light component removal column, and in the second distillation, the bottom effluent is distilled in a heavy component removal column under reduced pressure conditions to obtain a distillate comprising cyclohexylcarboxylic acid from the top of the heavy component removal column.

The first distillation is used to remove light components from the second hydrogenation mixture. In the first distillation, an operating pressure at the top of the light component removal column is preferably −0.02 MPa to −0.09 MPa, and the operating temperature at the bottom of the light component removal column is preferably 50-70° C., the pressures being a gauge pressure. In the second distillation, an operating pressure at the top of the heavy component removal column is −0.09 MPa to −0.095 MPa, and the operating temperature at the bottom of the heavy component removal column of 150-165° C., the pressure being a gauge pressure. The heavy component removal column is preferably a falling film distillation column.

According to the method for the hydrogenation reaction of the present invention, the second hydrogenation mixture is preferably subjected to gas-liquid separation prior to being separated to a gas phase stream containing mainly hydrogen, and the gas phase stream containing hydrogen may be recycled for the hydrogenation reaction, preferably after being treated in a tail gas treatment system. A liquid phase stream obtained by the gas-liquid separation is separated to obtain cyclohexylcarboxylic acid.

According to the method for the hydrogenation reaction of the present invention, all the second hydrogenation mixture may be separated, or part of the second hydrogenation mixture may be separated. In one preferred embodiment, part of the second hydrogenation mixture is separated, and the remaining part of the second hydrogenation mixture is recycled to the first hydrogenation step to be in contact with the first hydrogenation catalyst together with fresh benzoic acid for a reaction. In this preferred embodiment, a part of the liquid phase stream obtained after the gas-liquid separation may be separated, and the remaining part of the liquid phase stream is recycled for the first hydrogenation step. The amount of the liquid phase stream recycled for the first hydrogenation step may be 60-90%, preferably 70-90 wt % based on the total weight of the liquid phase stream.

FIG. 1 shows a preferred embodiment of the method for the hydrogenation reaction according to the present invention. This preferred embodiment is described below with reference to FIG. 1. As shown in FIG. 1, benzoic acid is mixed with cyclohexanecarboxylic acid to form a hydrogenation feedstock solution containing benzoic acid, the hydrogenation feedstock solution is fed to a hydrogenation feedstock buffer tank 1, and metered and pressurized through a metering pump 2, and the pressurized hydrogenation feedstock solution is mixed with high pressure hydrogen metered through a flow controller 3 in a pipe to form a feedstock mixture. The feedstock mixture enters a main hydrogenation tubular reactor 4 from bottom to top to be subjected to a main hydrogenation reaction under the action of a main hydrogenation catalyst (i.e., a first hydrogenation catalyst), a first hydrogenation mixture obtained from a main hydrogenation reaction outlet is mixed with high-pressure supplemental hydrogen metered through a flow controller 5 in a pipe, and then the mixture enters a post-hydrogenation fixed bed reactor 6 from bottom to top to be subjected to a post-hydrogenation reaction under the action of a post-hydrogenation catalyst (i.e., a second hydrogenation catalyst) to obtain a second hydrogenation mixture. The second hydrogenation mixture is cooled by a condenser 7, and then enters a high-pressure separation tank 8 for gas-liquid separation, after a small amount of vaporization products entrained in the separated hydrogen is removed, the separated hydrogen enters a tail gas treatment system, the hydrogenation product solution enters a hydrogenation crude product tank 10 through a control valve 9, a part of the hydrogenation product is fed to a dosing system via a metering pump 11 to be cyclically fed to the main hydrogenation tubular reactor 4, and a part of the hydrogenation product is metered by a metering pump 12 to be fed to a light component removal column 13 to remove light components from the hydrogenation product and collect the light components are removed in a recovery tank 14, effluent at the bottom of the light component removal column 13 is fed to a heavy component removal column 16 by a pump 15 to remove heavy components from the hydrogenation product, and the hydrogenation product with light components and heavy components removed enters a product tank 17, and is then packaged.

Compared with the prior art, the catalyst according to the present invention has a reduced content of noble metal, thereby effectively reducing the cost of the catalyst; moreover, the hydrogenation catalyst according to the present invention has good low-temperature activity, and a better hydrogenation reaction effect can be obtained even when a hydrogenation reaction is carried out at a lower temperature. The method for the benzoic acid hydrogenation reaction according to the present invention can implement continuous and stable operation, simplify a process flow, improve the production efficiency, and realize continuous production of cyclohexylcarboxylic acid, with good and stable product quality.

The present invention will be described in detail below with reference to preparation examples, experimental examples and examples, but the scope of the present invention is not thereby limited.

In the following preparation examples and comparative preparation examples, the content of Ru and the content of an auxiliary component in a catalyst were determined by X-ray fluorescence spectroscopy, and the alkali metal content was determined by inductively coupled plasma emission spectroscopy.

In the following experimental examples and examples, a composition of a second hydrogenation mixture was determined by gas chromatography, and the feedstock conversion and product selectivity were calculated according to the measured composition data by using the following formulae, Feedstock conversion=(the molar amount of feedstocks added−the molar amount of the remaining feedstocks)/the molar amount of feedstocks added×100%; and Product selectivity=the molar amount of a product produced by a reaction/(the molar amount of feedstocks added−the molar amount of the remaining feedstocks)×100%.

In the following preparation examples, experimental examples, and examples, a pressure was a gauge pressure unless otherwise specified.

Preparation examples 1-10 were used to prepare the hydrogenation catalyst according to the present invention.

Preparation Example 1

(1) Activated carbon (purchased from Shenhua Group, with a specific surface area of 950 $m^2/g$) was impregnated with 25 mL of an aqueous sodium hydroxide solution at a temperature of 20° C. for 2 h, then the impregnated activated carbon was washed with deionized water until a pH of washing effluent water was 7.2, and the washed solid matter was dried at 100° C. for 10 h to obtain a modified carrier.

(2) The modified carrier prepared in the step (1) was impregnated with 25 mL of an aqueous solution comprising $RuCl_3$ and $NiCl_2$ at a temperature of 50° C. for 15 h, and the impregnated modified carrier was dried at 80° C. for 20 h, and then calcined at 180° C. for 10 h in an air atmosphere to obtain a catalyst precursor. Wherein in the aqueous solution employed in the step (2), the concentration of $RuCl_3$ was $3.68 \times 10^{-5}$ mol/mL, and the concentration of $NiCl_2$ was $3.45 \times 10^{-5}$ mol/mL, and a molar ratio of NaOH employed in the step (1) to the total amount of Ru and Ni in the step (2) was 3:1.

(3) The catalyst precursor prepared in the step (2) was placed in an aqueous solution of hydrazine hydrate (a molar ratio of hydrazine hydrate to the total amount of Ru and Ni was 4:1, hydrazine hydrate is calculated by hydrazine) to be subjected to a reaction at a temperature of 60° C. for 4 h, filtration was carried out, and a solid matter collected was washed with deionized water for three times, and then dried at a temperature of 80° C. for 8 h in an air atmosphere to obtain the hydrogenation catalyst according to the present invention with a specific composition shown in Table 1.

Comparative Preparation Example 1

A hydrogenation catalyst was prepared by the same method as that in Preparation example 1, except that an aqueous solution used in the step (2) did not contain $NiCl_2$. A composition of the prepared hydrogenation catalyst is listed in Table 1.

Comparative Preparation Example 2

A hydrogenation catalyst was prepared by the same method as that in Preparation example 1, except that an aqueous solution used in the step (2) did not contain $RuCl_3$. A composition of the prepared hydrogenation catalyst is listed in Table 1.

Comparative Preparation Example 3

A hydrogenation catalyst was prepared by the same method as that in Preparation example 1, except that the step (1) was not carried out, and the activated carbon used in the step (1) of Preparation example 1 was directly used in the step (2). A composition of the prepared hydrogenation catalyst is listed in Table 1.

Preparation Example 2

A hydrogenation catalyst was prepared by the same method as that in Preparation example 1, except that in the step (2), calcination was performed at a temperature of 300° C. A composition of the prepared hydrogenation catalyst is listed in Table 1.

Preparation Example 3

A hydrogenation catalyst was prepared by the same method as that in Preparation example 1, except that the concentration of $NiCl_2$ in an aqueous solution used in the step (2) was $6.9 \times 10^{-5}$ mol/mL. A composition of the prepared hydrogenation catalyst is listed in Table 1.

Preparation Example 4

A hydrogenation catalyst was prepared by the same method as that in Preparation example 1, except that in the step (1), the concentration of sodium hydroxide in the aqueous sodium hydroxide solution was changed so that a molar ratio of NaOH used in the step (1) to the total amount of Ru and Ni in the step (2) was 1.5:1. A composition of the prepared hydrogenation catalyst is listed in Table 1.

Preparation Example 5

A hydrogenation catalyst was prepared by the same method as that in Preparation example 1, except that in the step (3), an equimolar amount of sodium borohydride was used as a reducing agent. A composition of the prepared hydrogenation catalyst is listed in Table 1.

Preparation Example 6

(1) Silicon oxide (purchased from Zibo Hengqi Powder New Material Co., Ltd., with a specific surface area of 180 $m^2/g$) was impregnated with 25 mL of an aqueous potassium hydroxide solution at a temperature of 60° C. for 2 h, then the impregnated silicon oxide was washed with deionized water until a pH of washing effluent water was 7.4, and the washed solid matter was dried at 120° C. for 5 h to obtain a modified carrier.

(2) The modified carrier prepared in the step (1) was impregnated with 25 mL of an aqueous solution containing ruthenium nitrate, ruthenium acetate and cobalt acetate at a temperature of 60° C. for 15 h, and the impregnated modified carrier was dried at 110° C. for 10 h, and then calcined at 250° C. for 2 h in an air atmosphere to obtain a catalyst precursor. Wherein in the aqueous solution used in the step (2), the concentration of ruthenium nitrate was $5.94 \times 10^{-5}$ mol/mL, the concentration of ruthenium acetate was $5.94 \times 10^{-5}$ mol/mL, and the concentration of cobalt acetate was $2.04 \times 10^{-6}$ mol/mL, and a molar ratio of KOH used in the step (1) to the total amount of Ru and Co in the step (2) was 5:1.

(3) The catalyst precursor prepared in the step (2) was placed in an aqueous solution of sodium borohydride (a molar ratio of sodium borohydride to the total amount of Ru and Co was 5:1) to be subjected to a reaction at a temperature of 50° C. for 5 h, filtration was carried out, and a solid matter collected was washed with deionized water for three times, and then dried at a temperature of 80° C. in an air atmosphere for 8 h to obtain the hydrogenation catalyst according to the present invention with a specific composition shown in Table 1.

Comparative Preparation Example 4

A hydrogenation catalyst was prepared by the same method as that in Preparation example 6, except that the step (1) was not carried out, and silicon oxide used in the step (1) of Preparation example 6 was directly used in the step (2). A composition of the prepared hydrogenation catalyst is listed in Table 1.

Comparative Preparation Example 5

A hydrogenation catalyst was prepared by the same method as that in Preparation example 6, except that in the step (2), the calcination was performed at a temperature of 300° C. A composition of the prepared hydrogenation catalyst is listed in Table 1.

Preparation Example 7

A hydrogenation catalyst was prepared by the same method as that in Preparation example 6, except that in the step (3), sodium borohydride was replaced with an equimolar amount of formaldehyde. A composition of the prepared hydrogenation catalyst is listed in Table 1.

Preparation Example 8

(1) Zirconium oxide (purchased from Zibo Qimingxing New Material Incorporated Co., Ltd., with a specific surface area of 120 $m^2/g$) was impregnated with 50 mL of an aqueous sodium hydroxide solution at a temperature of 50° C. for 4 h, then the impregnated zirconium oxide was washed with deionized water until a pH of washing effluent water was 7.5, and the washed solid matter was dried at 80° C. for 14 h to obtain a modified carrier.

(2) The modified carrier prepared in the step (1) was impregnated with 25 mL of an aqueous solution containing ruthenium nitrate and iron nitrate at a temperature of 40° C. for 20 h, and the impregnated modified carrier was dried at 120° C. for 8 h, and then calcined at 150° C. in an air atmosphere for 6 h to obtain a catalyst precursor. Wherein in the aqueous solution used in the step (2), the concentration of ruthenium nitrate was $1.19\times10^{-5}$ mol/mL, and the concentration of iron nitrate is $2.15\times10^{-4}$ mol/mL, and a molar ratio of NaOH used in the step (1) to the total amount of Ru and Fe in the step (2) was 5:1.

(3) The catalyst precursor prepared in the step (2) was placed in an aqueous solution containing hydrazine hydrate and formaldehyde (a molar ratio of the total amount of hydrazine hydrate and formaldehyde to the total amount of Ru and Fe was 6:1, and a molar ratio of hydrazine hydrate to formaldehyde was 1:4, hydrazine hydrate is calculated by hydrazine) to be subjected to a reaction at a temperature of 20° C. for 10 h, filtration was carried out, and a solid matter collected was washed with deionized water for three times, and then dried at a temperature of 70° C. in an air atmosphere for 10 h to obtain the hydrogenation catalyst according to the present invention with a specific composition shown in Table 1.

Preparation Example 9

A hydrogenation catalyst was prepared by the same method as in Preparation example 8, except that in the step (3), an aqueous reducing agent solution did not contain hydrazine hydrate (i.e., hydrazine hydrate was replaced with an equimolar amount of formaldehyde, and a total molar amount of a reducing agent was the same as that in Preparation example 8). A composition of the prepared hydrogenation catalyst is listed in Table 1.

Comparative Preparation Example 6

A hydrogenation catalyst was prepared by the same method as in Preparation example 8, except that the step (1) was not carried out, and zirconium oxide used in the step (1) of Preparation example 8 was directly used in the step (2). A composition of the prepared hydrogenation catalyst is listed in Table 1.

Preparation Example 10

(1) Titanium oxide (purchased from Zibo Hengqi Powder New Material Co., Ltd., with a specific surface area of 120 $m^2/g$) was impregnated with 50 mL of an aqueous lithium hydroxide solution at a temperature of 40° C. for 8 h, then the impregnated titanium oxide was washed with deionized water until a pH of washing effluent water was 7.3, and the washed solid matter was dried at 110° C. for 6 h to obtain a modified carrier.

(2) The modified carrier prepared in the step (1) was impregnated with 25 mL of an aqueous solution containing ruthenium nitrate and nickel nitrate at a temperature of 80° C. for 20 h, and the impregnated modified carrier was dried at 100° C. for 12 h, and then calcined at 200° C. for 5 h in an air atmosphere to obtain a catalyst precursor. Wherein in the aqueous solution used in the step (2), the concentration of ruthenium nitrate was $5.94\times10^{-5}$ mol/mL, and the concentration of nickel nitrate was $6.89\times10^{-5}$ mol/mL, and a molar ratio of LiOH used in the step (1) to the total amount of Ru and Ni in the step (2) was 4:1.

(3) The catalyst precursor prepared in the step (2) was placed in an aqueous formaldehyde solution (a molar ratio of formaldehyde to the total amount of Ru and Ni was 3:1) to be subjected to reaction at a temperature of 80° C. for 1 h, filtration was carried out, and a solid matter collected was washed with deionized water for three times, and then dried at a temperature of 70° C. in an air atmosphere for 10 h to obtain the hydrogenation catalyst according to the present invention with a specific composition shown in Table 1.

TABLE 1

| No. | Ru (w t%) | Auxiliary component/ content (wt %) | Alkali metal/content (ppm, by weight) | Carrier |
|---|---|---|---|---|
| Preparation example 1 | 0.8 | Ni/0.5 | Na/200 | Activated carbon |
| Comparative preparation example 1 | 0.8 | None | Na/200 | Activated carbon |
| Comparative preparation example 2 | None | Ni/0.5 | Na/200 | Activated carbon |
| Comparative preparation example 3 | 0.8 | Ni/0.5 | None | Activated carbon |
| Preparation example 2 | 0.8 | Ni/0.5 | Na/200 | Activated carbon |
| Preparation example 3 | 0.8 | Ni/1 | Na/200 | Activated carbon |
| Preparation example 4 | 0.8 | Ni/0.5 | Na/100 | Activated carbon |

TABLE 1-continued

| No. | Ru (w t%) | Auxiliary component/ content (wt %) | Alkali metal/content (ppm, by weight) | Carrier |
|---|---|---|---|---|
| Preparation example 5 | 0.8 | Ni/0.5 | Na/200 | Activated carbon |
| Preparation example 6 | 3 | Co/0.3 | K/380 | Silicon oxide |
| Comparative preparation example 4 | 3 | Co/0.3 | None | Silicon oxide |
| Comparative preparation example 5 | 3 | Co/0.3 | K/380 | Silicon oxide |
| Preparation example 7 | 3 | Co/0.3 | K/380 | Silicon oxide |
| Preparation example 8 | 0.3 | Fe/3 | Na/550 | Zirconium oxide |
| Preparation example 9 | 0.3 | Fe/3 | Na/550 | Zirconium oxide |
| Comparative preparation example 6 | 0.3 | Fe/3 | None | Zirconium oxide |
| Preparation example 10 | 1.5 | Ni/1 | Li/240 | Titanium oxide |

Experimental examples 1-12 were used to evaluate the catalytic performance of a hydrogenation catalyst employed according to the method of the present invention.

Experimental Examples 1-12

(1) Charging of Hydrogenation Catalyst

The bottom of a tubular fixed bed hydrogenation reactor was first charged with a bottom layer of inert porcelain balls for support, then a hydrogenation catalyst was charged on the porcelain balls in a random stack, wherein a ratio of a charging height of the hydrogenation catalyst to a tube diameter of a reaction tube in the tubular fixed bed hydrogenation reactor was 10:1, and finally a top layer of inert porcelain balls was charged at the upper part of a bed layer, and a reactor top head was installed.

(2) Supplemental Reduction

Hydrogen was introduced into the tubular fixed bed hydrogenation reactor, and a supplemental hydrogenation reaction was carried out under the conditions listed in Table 2.

(3) Hydrogenation Reaction

A benzoic acid solution (a solvent was cyclohexanecarboxylic acid) was introduced into the tubular fixed bed hydrogenation reactor, and a hydrogenation reaction was continued to be carried out for 72 h under the conditions listed in Table 3. The compositions of reaction products output from the tubular fixed bed hydrogenation reactor were determined, and the conversion of benzoic acid and selectivity of cyclohexylcarboxylic acid were calculated. The results are listed in Table 3.

Comparative Experimental Examples 1-3

Cyclohexylcarboxylic acid was prepared by the same method as that in Experimental example 1, except for the hydrogenation catalysts prepared in Comparative preparation examples 1-3, were respectively used, and the experimental results are listed in Table 3.

Comparative Experimental Examples 4-5

Cyclohexylcarboxylic acid was prepared by the same method as that in Experimental example 6, except for the hydrogenation catalysts prepared in Comparative preparation examples 4-5 were respectively used, and the experimental results are listed in Table 3.

Comparative Experimental Example 6

Cyclohexylcarboxylic acid was prepared by the same method as that in Experimental example 9, except for the hydrogenation catalyst prepared in Comparative preparation example 6 was used, and the experimental results are listed in Table 3.

TABLE 2

| No. | Supplemental reduction temperature (° C.) | Supplemental reduction pressure (MPa) | Supplemental reduction time (h) |
|---|---|---|---|
| Experimental example 1 | 150 | 3 | 10 |
| Comparative experimental example 1 | | | |
| Comparative experimental example 2 | | | |
| Comparative experimental example 3 | | | |
| Experimental example 2 | | | |
| Experimental example 3 | | | |
| Experimental example 4 | | | |
| Experimental example 5 | | | |
| Experimental example 6 | 160 | 3 | 4 |
| Comparative experimental example 4 | | | |
| Comparative experimental example 5 | | | |
| Experimental example 7 | | | |
| Experimental example 8 | 150 | 2 | 10 |
| Experimental example 9 | | | |
| Comparative experimental example 6 | | | |
| Experimental example 10 | 120 | 2 | 4 |
| Experimental example 11 | 100 | 3 | 10 |
| Experimental example 12 | 180 | 5 | 6 |

Experimental results of Experimental examples 1-12 confirmed that the hydrogenation catalyst according to the present invention has good low-temperature activity, and a good hydrogenation reaction effect can be obtained even when the hydrogenation reaction is carried out at a relatively low temperature.

TABLE 3

| No. | Catalyst source | Hydrogenation reaction Feed concentration wt % | Temperature ° C. | Pressure MPa | Space velocity $h^{-1}$ | Molar ratio of hydrogen to acid mol:mol | Analytical data Conversion % | Selectivity % |
|---|---|---|---|---|---|---|---|---|
| Experimental example 1 | Preparation example 1 | 10 | 120 | 5 | 1.8 | 50 | 99.95 | 98.9 |
| Comparative experimental example 1 | Comparative preparation example 1 | | | | | | 86.1 | 85.1 |
| Comparative experimental example 2 | Comparative preparation example 2 | | | | | | 75.2 | 77.0 |
| Comparative experimental example 3 | Comparative preparation example 3 | | | | | | 89.9 | 87.8 |
| Experimental example 2 | Preparation example 2 | | | | | | 91.0 | 90.8 |
| Experimental example 3 | Preparation example 3 | | | | | | 93.9 | 92.1 |
| Experimental example 4 | Preparation example 4 | | | | | | 94.8 | 93.2 |
| Experimental example 5 | Preparation example 5 | | | | | | 95.0 | 94.6 |
| Experimental example 6 | Preparation example 6 | 30 | 80 | 2 | 1 | 4.0 | 99.9 | 98.3 |
| Comparative experimental example 4 | Comparative preparation example 4 | | | | | | 89.7 | 88.5 |
| Comparative experimental example 5 | Comparative preparation example 5 | | | | | | 91.8 | 90.3 |
| Experimental example 7 | Preparation example 7 | | | | | | 95.8 | 94.5 |
| Experimental example 8 | Preparation example 8 | 20 | 100 | 4 | 1.2 | 10 | 99.96 | 98.6 |
| Experimental example 9 | Preparation example 9 | | | | | | 94.9 | 93.7 |
| Comparative experimental example 6 | Comparative preparation example 6 | | | | | | 91.8 | 90.5 |
| Experimental example 10 | Preparation example 10 | 40 | 60 | 4 | 0.5 | 7 | 99.2 | 98.7 |
| Experimental example 11 | Preparation example 1 | 25 | 90 | 1 | 0.5 | 6 | 99.6 | 98.8 |
| Experimental example 12 | Preparation example 8 | 15 | 70 | 3.5 | 2 | 20 | 99.0 | 98.5 |

Examples 1-7

Examples 1-7 used the method shown in FIG. 1 for a hydrogenation reaction of benzoic acid, and a specific operation process was as follows.

1. Charging and Activation of Hydrogenation Catalyst

Taking a tubular reactor as an example for illustration, a post-hydrogenation fixed bed reactor was charged with a catalyst in the same way as that of the tubular reactor.

First, an outlet head was installed at the bottom of the reactor, inert porcelain balls were charged on the outlet head for supporting and material preheating, and then hydrogenation catalyst was charged on the porcelain balls in a random stack, and finally, inert porcelain balls were charged at the upper part of a bed layer, and a reactor top head was installed, and supplemental reduction was performed by using the first hydrogenation catalyst and the second hydrogenation catalyst by the same method as that in Experimental example 1.

2. Hydrogenation Reaction

As shown in FIG. 1, benzoic acid was mixed with cyclohexanecarboxylic acid to form a hydrogenation feedstock solution containing benzoic acid, the hydrogenation feedstock solution was fed to a hydrogenation feedstock buffer tank 1, and metered and pressurized through a metering pump 2, and the pressurized hydrogenation feedstock solution was mixed with high pressure hydrogen metered through a flow controller 3 in a pipe to form a feedstock mixture. The feedstock mixture entered a main hydrogenation tubular reactor 4 from bottom to top to be subjected to a main hydrogenation reaction under the action of main hydrogenation catalyst (i.e., first hydrogenation catalyst), first hydrogenation mixture obtained from main hydrogenation reaction outlet was mixed with high-pressure supplemental hydrogen metered through a flow controller 5 in a pipe, and then the mixture entered post-hydrogenation fixed bed reactor 6 from bottom to top to be subjected to post-hydrogenation reaction under the action of post-hydrogenation catalyst (i.e., second hydrogenation catalyst) to obtain second hydrogenation mixture.

3. By-Product Removal

The second hydrogenation mixture was cooled by condenser 7, and then entered high-pressure separation tank 8 for gas-liquid separation, after a small amount of vaporization products entrained in the separated hydrogen was removed, the separated hydrogen entered a tail gas treatment system, the separated hydrogenation product solution entered hydrogenation crude product tank 10 through control valve 9, a part of the hydrogenation product was fed to a dosing system via a metering pump 11 to be cyclically fed to the main hydrogenation tubular reactor 4, and a part of the hydrogenation product was metered by a metering pump 12 to be fed to a light component removal column 13 to remove light components from the hydrogenation product and collect the light components in a recovery tank 14, effluent at the bottom of the light component removal column 13 was fed to a heavy component removal column 16 by a pump 15 to remove heavy components from the hydrogenation product, and the hydrogenation product with light components and heavy components removed entered a product tank 17, and was then packaged.

In Examples 1-7, cyclohexylcarboxylic acid was prepared by respectively subjecting benzoic acid to hydrogenation reaction under the conditions listed in Table 4, and performing separation under the conditions listed in Table 5 according to the above operation process.

The experimental results of Examples 1-7 confirmed that the preparation method for cyclohexylcarboxylic acid according to the present invention can implement continuous and stable operation, simplify a process flow, improve the production efficiency, and realize continuous production of cyclohexylcarboxylic acid, with good and stable product quality.

Preferred embodiments of the present invention are described in detail above, but the present invention is not limited thereto. Within the scope of the technical idea of the present invention, many simple variations can be made to the technical solution of the present invention, including combinations of the technical features in any other suitable manner, and these simple variations and combinations should also be regarded as the contents disclosed in the present invention, and all fall within the protection scope of the present invention.

TABLE 4

| | Main hydrogenation tubular reactor | | | | | | Post-hydrogenation fixed bed reactor |
|---|---|---|---|---|---|---|---|
| No. | First hydrogenation catalyst | Feed concentration (%) | Temperature (° C.) | Pressure (MPa) | Space velocity ($h^{-1}$) | Hydrogen to acid ratio (mol) | Second hydrogenation catalyst |
| Example 1 | Preparation example 1 | 20 | 70 | 4 | 5 | 2.8 | Preparation example 1 |
| Example 2 | Preparation example 6 | 10 | 90 | 5 | 4.5 | 3.0 | Preparation example 6 |
| Example 3 | Preparation example 8 | 30 | 85 | 2 | 0.5 | 2.4 | Preparation example 8 |
| Example 4 | Preparation example 10 | 40 | 60 | 4 | 1.2 | 2.9 | Preparation example 10 |
| Example 5 | Preparation example 1 | 25 | 82 | 1 | 0.5 | 2.5 | Preparation example 8 |
| Example 6 | Preparation example 6 | 15 | 65 | 3.5 | 6 | 4.0 | Preparation example 10 |

| | Post-hydrogenation fixed bed reactor | | | | Analytical data | |
|---|---|---|---|---|---|---|
| No. | Temperature (° C.) | Pressure (MPa) | Space velocity ($h^{-1}$) | Hydrogen to acid ratio (mol) | Conversion (%) | Selectivity (%) |
| Example 1 | 90 | 4 | 0.8 | 2.2 | 99.92 | 98.9 |
| Example 2 | 110 | 5 | 2.2 | 1.0 | 99.9 | 98.3 |
| Example 3 | 100 | 2 | 3 | 2.4 | 99.89 | 98.6 |
| Example 4 | 80 | 4 | 0.5 | 0.5 | 99.89 | 98.6 |
| Example 5 | 120 | 1 | 2.5 | 3.0 | 99.9 | 98.1 |
| Example 6 | 110 | 3.5 | 0.6 | 2.2 | 99.9 | 98.5 |

TABLE 5

| No. | Amount of liquid phase stream recycled for a first hydrogenation step based on the total weight of the liquid phase stream (%) | Light component removal column: Column bottom temperature (° C.) | Light component removal column: Column top pressure (MPa, gauge pressure) | Heavy component removal column: Column bottom temperature (° C.) | Heavy component removal column: Column top pressure (MPa, gauge pressure) | Product purity (%) |
|---|---|---|---|---|---|---|
| Example 1 | 80 | 55 | −0.09 | 155 | −0.095 | 99.8 |
| Example 2 | 90 | 70 | −0.02 | 160 | −0.095 | 99.9 |

TABLE 5-continued

| No. | Amount of liquid phase stream recycled for a first hydrogenation step based on the total weight of the liquid phase stream (%) | Light component removal column: Column bottom temperature (° C.) | Light component removal column: Column top pressure (MPa, gauge pressure) | Heavy component removal column: Column bottom temperature (° C.) | Heavy component removal column: Column top pressure (MPa, gauge pressure) | Product purity (%) |
|---|---|---|---|---|---|---|
| Example 3 | 70 | 50 | −0.06 | 150 | −0.095 | 99.6 |
| Example 4 | 60 | 58 | −0.04 | 158 | −0.095 | 99.7 |
| Example 5 | 75 | 62 | −0.08 | 165 | −0.09 | 99.9 |
| Example 6 | 85 | 61 | −0.08 | 161 | −0.09 | 99.7 |

The invention claimed is:

1. A method for performing a benzoic acid hydrogenation reaction, the method comprising a first hydrogenation step and a second hydrogenation step, wherein in the first hydrogenation step, benzoic acid and hydrogen are contacted with a first hydrogenation catalyst under conditions of the first hydrogenation reaction to obtain a first hydrogenation mixture; and in the second hydrogenation step, the first hydrogenation mixture and supplemental hydrogen are contacted with a second hydrogenation catalyst under conditions of the second hydrogenation reaction to obtain a second hydrogenation mixture;

wherein the first hydrogenation catalyst and the second hydrogenation catalyst are the same or different, and each independently comprise a carrier, an active component, an auxiliary component, and an alkali metal element supported on the carrier, wherein the active component is ruthenium, the content of the active component is 0.3-3 wt. %, the content of the auxiliary component is 0.3-3 wt. %, and the content of the alkali metal element is 10-1000 ppm by weight based on the total amount of the hydrogenation catalyst, wherein the contents of the active component, the auxiliary component, and the alkali metal element are each calculated as elemental content, wherein the auxiliary component is selected from the group consisting of:

(a) nickel, wherein the molar ratio of the auxiliary component to the active component is 0.5-1.5:1, and the carrier is activated carbon and/or titanium oxide;

(b) cobalt, wherein the molar ratio of the auxiliary component to the active component is 0.1-0.5:1, and the carrier is silicon oxide; and (c) iron, wherein the molar ratio of the auxiliary component to the active component is 10-25:1, and the carrier is zirconium oxide.

2. The method according to claim 1, wherein the first contacting is carried out in a tubular reactor, and the second contacting is carried out in a fixed bed reactor.

3. The method according to claim 1, wherein in the first hydrogenation step, a molar ratio of hydrogen to benzoic acid is 2.4-4:1.

4. The method according to claim 1, wherein in the second hydrogenation step, a molar ratio of the supplemental hydrogen to benzoic acid in the first hydrogenation step is 1-3:1.

5. The method according to claim 1, wherein the method further comprises a separation step in which the second hydrogenation mixture is separated to obtain cyclohexylcarboxylic acid.

6. The method according to claim 5, wherein the separation step comprises a first distillation and a second distillation, wherein in the first distillation, the second hydrogenation mixture is distilled in a light component removal column under reduced pressure conditions to obtain a distillate comprising light components from a top of the light component removal column, and a bottom effluent from a bottom of the light component removal column, and in the second distillation, the bottom effluent is distilled in a heavy component removal column under reduced pressure conditions to obtain distillate comprising cyclohexylcarboxylic acid from a top of the heavy component removal column.

7. The method according to claim 6, wherein in the first distillation, an operating pressure at the top of the light component removal column is −0.02 MPa to −0.09 MPa, and an operating temperature at the bottom of the light component removal column is 50-70° C., the pressure being a gauge pressure; and in the second distillation, an operating pressure at the top of the heavy component removal column is −0.09 MPa to −0.095 MPa, and an operating temperature at the bottom of the heavy component removal column is 150-165° C., the pressure being a gauge pressure.

8. The method according to claim 1, wherein the hydrogenation catalyst is prepared by a method comprising the following steps of:

(1) contacting a carrier with a solution comprising an alkali metal compound to obtain a modified carrier;

(2) contacting the modified carrier with a solution comprising an active component precursor and an auxiliary component precursor to obtain a supported carrier supported with the active component precursor and the auxiliary component precursor, removing at least part of volatile components from the supported carrier, and performing a calcination to obtain a hydrogenation catalyst precursor, wherein the calcination is carried out at a temperature of not higher than 300° C., the active component of the active component precursor is ruthenium, and an auxiliary component of the auxiliary component precursor is one or two or more selected from the group consisting of nickel, iron and cobalt; and (3) contacting the hydrogenation catalyst precursor with a reducing agent under the conditions of reduction reaction to obtain the hydrogenation catalyst.

9. The method according to claim 8, wherein the alkali metal compound is an alkali metal hydroxide.

10. The method according to claim 8, wherein in the step (1), the contacting is carried out at a temperature of 20-60° C.

11. The method according to claim 8, wherein in the step (2), the active component precursor is one or two or more selected from the group consisting of ruthenium chloride, ruthenium nitrate and ruthenium acetate; and the auxiliary component precursor is one or two or more selected from the group consisting of a nitrate of the auxiliary component, a sulfate of the auxiliary component, a formate of the auxiliary component, an acetate of the auxiliary component, and a chloride of the auxiliary component.

12. The method according to claim 8, wherein in the step (2), the calcination is carried out at a temperature of not higher than 250° C.

13. The method according to claim 8, wherein in terms of moles, a ratio of the reducing agent in the step (3) to (the active component in the step (2) + the auxiliary component in the step (2)) is 3-6:1.

14. The method according to claim 8, wherein the reducing agent is one or two or more selected from the group consisting of hydrazine hydrate, sodium borohydride and formaldehyde.

15. The method according to claim 8, wherein in the step (3), the contacting is carried out at a temperature of 20-80° C.

* * * * *